United States Patent [19]

Baucke et al.

[11] Patent Number: 5,071,528
[45] Date of Patent: Dec. 10, 1991

[54] METHOD AND DEVICE FOR MEASURING THE OXYGEN PARTIAL PRESSURE IN HIGH-TEMPERATURE, CORROSIVE LIQUIDS

[75] Inventors: Friedrich G. K. Baucke, Mainz; Gernot Roeth, Dalheim; Ralf-Dieter Werner, Laufersweiler, all of Fed. Rep. of Germany

[73] Assignee: Schott Glaswerke, Mainz, Fed. Rep. of Germany

[21] Appl. No.: 420,504

[22] Filed: Oct. 11, 1989

[51] Int. Cl.$^5$ .......................................... G01N 27/417
[52] U.S. Cl. .................. 204/153.18; 204/421; 204/422
[58] Field of Search .................... 204/153.18, 421–429

[56] References Cited

U.S. PATENT DOCUMENTS

| 3,464,008 | 8/1969 | Meysson et al. | 204/422 |
| 3,719,574 | 3/1973 | Richardson | 204/422 |

Primary Examiner—T. Tung
Attorney, Agent, or Firm—Millen, White & Zelano

[57] ABSTRACT

The invention relates to a measuring device to measure the oxygen partial pressure, in particular, glass melts, comprising a platinum measuring electrode and a reference electrode arrangement. The reference electrode arrangement is placed in an outer pipe and contains a platinum reference electrode. The electrode protrudes into an oxygen-conducting solid electrolyte, through which an oxygen-containing reference gas flows. For ion-conducting contact with the melt, a rod-shaped contact element of oxygen-ion conducting material is inserted into the open lower end of the outer pipe. This contact element is immersed in the melt. To prevent the inflow of environmental vapors into the measuring space through leaks at this connecting point, the actual measuring arrangement is placed in a liner pipe of oxygen-ion conducting material whose lower end is in ion-conducting contact with the contact element by way of an oxygen-ion conducting powdered material. Additionally, the annular space around the liner pipe can be separated from the interior of the liner pipe, and a flow of inert gas can be provided through the annular space via gas inlet and outlet connections.

25 Claims, 2 Drawing Sheets

METHOD AND DEVICE FOR MEASURING THE OXYGEN PARTIAL PRESSURE IN HIGH-TEMPERATURE, CORROSIVE LIQUIDS

RELATED U.S. APPLICATION

This application is related to copending U.S. Application Ser. No. 07/420,496, filed even date herewith.

BACKGROUND OF THE INVENTION

The invention relates to a measuring device and method for measuring the oxygen partial pressure in high-temperature, corrosive liquids, in particular, glass and salt melts.

Measuring devices of this kind are known, for example, from DE-PS 31 09 454. Platinum electrodes are generally used as both measuring and reference electrodes. As oxygen-ion conducting solid electrolyte, there is used an oxidic material, generally zirconium dioxide ($ZrO_2$), provided, if necessary, with suitable doping, for example, doped with a second oxide, usually yttrium oxide ($Y_2O_3$). The doping material increases the ion conductivity of the solid electrolyte basic material. The zirconium dioxide doped in this way exhibits an oxygen-ion transport number of 1, which means that the only ions mobile in the electrolyte are oxygen ions.

To obtain a good three-phase contact in the reference electrode arrangement, advantageously, an amount of powdered or granular loose solid electrolyte is brought into the reference space. The platinum reference electrode and the outlet of a reference gas feed pipe extend into this powdered solid electrolyte. At the high temperatures present with glass melts, the solid electrolyte powder sinters during first use so that a gas-permeable, sintered compact is formed that is very suitable as a three-phase contact zone. On this aspect, see also DE-PS 30 28 270. The term "three-phase" contact zone refers to the mutual contact of three elements, i.e., phases. These elements are the platinum electrode wire, the sintered solid electrolyte material, and the reference gas (oxygen).

For external contact of the solid electrolyte with the liquid or melt, there is used a pipe made from oxygen ionizing solid electrolyte, which is closed at the lower end. This pipe, which contains the reference space, is immersed overall in the liquid or melt. The sintered compact of the oxygen-ion conducting electrolyte is placed in the lower, closed end of the pipe and is in direct contact with the wall material of the pipe. In this way, a direct conduction of oxygen ions through the wall of the lower pipe end into the powdered material or sintered compact, and thus into the three-phase contact area, is guaranteed. The other advantage of directly immersing this arrangement into the liquid is that the temperatures at the measuring electrode and at the reference electrode arrangement, which are both immersed into the liquid, can be considered to be approximately the same. A temperature compensation of the measuring voltage obtained with the measuring arrangement is generally not required in this case.

The general functioning of the prior art devices as described herein has been explained by the inventor in his publication, "Development of Electrochemical Cells Employing Oxide Ceramics for Measuring Oxygen Partial Pressures in Laboratory and Technical Glass Melts" [Glastechn. Ber. 56K (1983) Bd. 1].

But a drawback of this arrangement is that, in particular with corrosive, lead-containing glass melts, the pipe made of the solid electrolyte material in the flowing melt is so extensively corroded that it possesses a service life of, at most, one week. Therefore, due to the penetration into glass melt, expensive reference electrodes are useless and have to be rejected.

This drawback is overcome, for example, by using a special contact element in the form of an elongated rod made of oxygen-ion conducting material which is positioned with its upper end in ion-conducting contact with the solid electrolyte in the reference space of the reference electrode arrangement. Only the lower end of the contact element is immersed in the melt. To the extent that corrosion wear of the immersed end of the oxygen-ion conducting rod occurs, the position of the whole reference electrode arrangement can be reset so as to maintain immersion in the melt until the rod is mostly used up. In this way, not only are considerably increased service lives achieved; but, with a suitable embodiment, the spent rod can also be replaced by a new one so that the same reference electrode arrangement can continue to be used. This embodiment can be manufactured less expensively because the outer pipe enclosing the reference space need no longer be made of expensive solid electrolyte material. Instead, the outer pipe can be made, for example, of a material which is neutral to oxygen ion conduction and which is heat resistant, such as aluminum oxide. Reference electrode embodiments of this kind are described in DE-PS 31 09 454.

An embodiment of a reference electrode arrangement, as described in DE-GM 85 13 976, where a rod-like contact element of oxygen-ion conducting material is provided with only its lower end immersed in the melt and exposed to corrosion by the latter, has proven to be effective. With this embodiment, the reference space is in a pipe, made of a highly heat-resistant material and which is open at its lower end, into whose lower end the rodlike contact element is inserted a short distance and held, for example, with a crossbolt.

This embodiment offers in itself the advantage that the contact element, after extensive use, can be exchanged for a new one so that the rest of the relatively expensive reference electrode arrangement can be re-used.

But here a problem is presented regarding sufficient sealing of the contact element inside the outer pipe of the measuring arrangement into which it is inserted. Namely, there is the danger that gases and vapors from the atmosphere above the liquid or melt will invade the three-phase contact zone through a remaining gap between the contact element and outer pipe and thereby change the composition of the reference gas, leading to faulty measurements. Attempts have been made to correct this problem by increasing the pressure of the reference gas inside the measuring arrangement so that the reference gas is discharged through the leaks, rather than gases penetrating into the measuring arrangement from the outside. But this solution has proven to be unreliable.

SUMMARY OF THE INVENTION

An object of the invention is to provide a device of the kind described above and a method of using same which exhibit greater certainty that little or no gases and vapors from the environment above the liquid or melt can penetrate into the three-phase contact area used for the reference measurement.

Upon further study of the specification and appended claims, further objects and advantages of this invention will become apparent to those skilled in the art.

These objects are achieved according to the invention by a measuring device for measuring the oxygen partial pressure in high-temperature, corrosive liquids comprising:

a measuring electrode adapted for immersion into a corrosive liquid;

a reference electrode arrangement containing a reference space which is enclosed by an outer pipe made of highly heat-resistant material, the reference electrode arrangement also containing a reference electrode, a solid electrolyte of oxygen-ion conducting material, means for introducing a reference gas with defined oxygen content into the reference space, thereby forming a three-phase contact, and a contact element with its upper end inserted in the lower, open end of the outer pipe and held there by fastening means, the contact element being adapted for immersion into a corrosive liquid and being made of oxygen-ion conducting material, and the contact element is in oxygen-ion conducting contact with the solid electrolyte in the reference space;

a liner pipe closed at its lower end and positioned within the outer pipe, the liner pipe contains the reference space and is made of oxygen-ion conducting material; and an amount of oxygen-ion conducting, powdered material positioned on the upper end of the contact element inserted in the outer pipe, the powdered material being in oxygen-ion conducting contact with the contact element and the lower end of said liner pipe.

Through the use of a liner pipe, which is closed at its lower end and is made of oxygen-ion conducting material, and in which the actual measuring arrangement, namely the three-phase contact zone is placed, assembly gaps that lead into the actual measuring arrangement are prevented. In this way, gases and vapors from the environment cannot reach the three phase contact zone, provided, of course, that the entire arrangement is also closed on top with a sealing cover.

Providing another pipe of oxygen-ion conducting ceramic does result in the measuring cell becoming somewhat more expensive. However, this is not so important since the overall measuring arrangement can be reused after corrosion of the rodlike contact element by replacing the latter. Thus, the measuring arrangement does not become unusable. Earlier measuring arrangements in which the pipe, closed at its lower end and made of oxygen-ion conducting ceramic, was directly immersed in the liquid or melt, did become unusable.

The ion-conducting contact with the embodiment according to the invention takes place through the rodlike contact element, through the optionally sintered powdered material between contact element and liner pipe and through the wall of the liner pipe into the optionally, also sintered solid electrolyte in the three-phase contact zone. All four elements are suitable made of the same oxygen-ion conducting ceramic material, namely zirconium oxide doped with yttrium oxide. The only important detail to which attention should be paid is to assure that good mechanical contact exists among the individual material sections. While the rodlike contact element and the liner pipe are made of a ceramic in the sintered state, the solid electrolyte and the material between the liner pipe and the contact element are initially fed in as a powder or fine granulate. This will guarantee a good mechanical contact between the solid parts. The powdered material then sinters into a porous, but oxygen-ion conducting, body when the measuring arrangement is brought under the effect of the high temperatures.

The prevention of penetration of the environmental air and vapors into the measuring arrangement can be further assured according to the invention in a preferred embodiment of the measuring device wherein the flow of the reference gas is conveyed in a suitable way and where possibly an inert gas flow is additionally provided through certain areas.

For a good three-phase contact in the measuring zone, it is suitable, as already represented in DE-GM 85 13 976, to insert the end of the feed pipe for the reference gas into the solid electrolyte in the actual measuring zone. After passing through the porous solid electrolyte, the gas then flows outside the feed pipe back upward and out of the measuring arrangement. Such an arrangement of the measuring device according to the invention is preferred.

Starting with such an arrangement, in a first embodiment according to the invention, the outer pipe of the measuring arrangement is closed by a cover on top, except for the various required passages. However, the liner pipe is open on top inside the outer pipe, and there is a space between the top edge of the liner pipe and the cover of the outer pipe. The reference gas introduced into the lower measuring area of the liner pipe flows into the liner pipe, then back upward to fill the outer annular space between liner pipe and outer pipe. The discharge pipe for the reference gas is in the upper area, preferably in the cover, of the outer pipe. If the reference gas in the measuring arrangement is kept at an appropriate pressure, it can additionally prevent gas and vapors from the outside from penetrating, through any remaining leaks, into the annular space between liner pipe and outer pipe.

This embodiment can be further improved by providing a liner pipe having a closed upper end inside the outer pipe and providing a reference gas inlet pipe which runs through the upper closure of the liner pipe. The discharge end of the reference gas inlet pipe extends downward into the powdered, oxygen-ion conducting material between liner pipe and contact element. In this way, the reference gas, after leaving the measuring arrangement in the liner pipe, is conveyed directly to the point where leaks still could exist. The outlet for the reference gas is suitably in the cover of the outer pipe here, too.

In another preferred embodiment, the interior of the liner pipe and the annular space surrounding the latter are completely separated from one another. The reference gas is conveyed directly out of the interior of the liner pipe at the annular space between inner pipe and outer pipe there are provided connections for introducing and removing an inert protective gas, for example, argon. Here, the feed pipe for the protective gas is run in this embodiment, too, suitable with its discharge end reaching up into the powdered material between liner pipe and contact element. The outlet connection for the inert gas can be in the upper area of the annular space.

For all embodiments, the discharging gases can be conveyed through transparent bubble counters. These bubble counters can be monitored to determine if the gas, in fact, is being discharged from the measuring arrangement or is disappearing in another way through a possible leak. Such counters can, therefore, provide a first indication that environmental air may be penetrating into the measuring arrangement.

Besides platinum, other suitable materials for the electrodes include palladium (Pd) and rhodium (Rh).

Suitable oxygen-ion conducting materials include $ZrO_2$, $ThO_2$, and $HfO_2$.

In addition, the oxygen-ion conducting material can be doped with a suitable dopant such as $Y_2O_3$, CaO, or MgO.

The outer pipe is generally made of a suitable refractory material, for example, $Al_2O_3$, MgO, or "Zac", a zirconium aluminum oxide.

Generally, the oxygen-ion conducting material should exhibit an oxygen-ion transport number which essentially equals 1.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

BRIEF DESCRIPTION OF THE DRAWINGS

Various other objects, features, and attendant advantages of the present invention will be more fully appreciated as the same becomes better understood when considered in conjunction with the accompanying drawings, in which like reference characters designate the same or similar parts throughout the several views and wherein.

DETAILED DESCRIPTION

Figure 1:
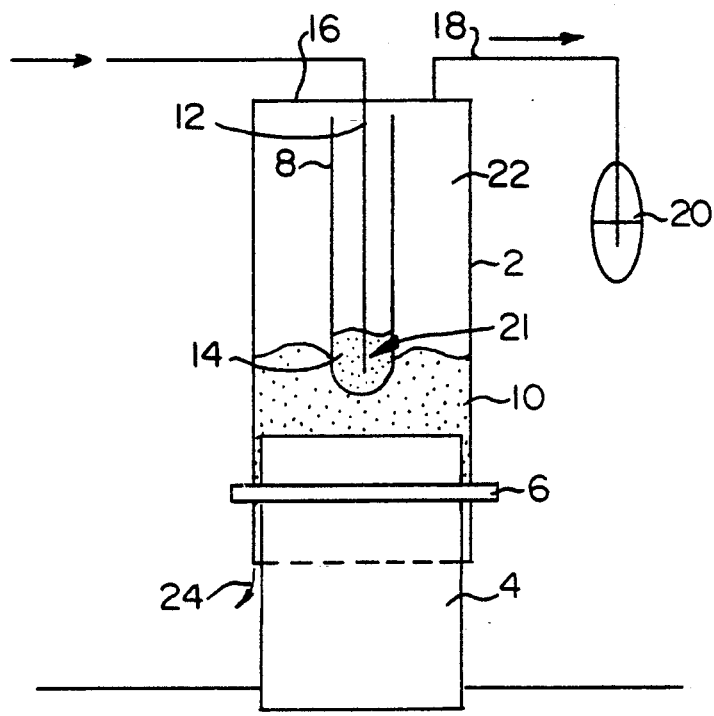
FIG. 1, in diagrammatic side view, illustrates a first embodiment of a reference electrode arrangement for a measuring device to measure the oxygen partial pressure in high-temperature, corrosive liquids.

The reference electrode arrangement represented in diagrammatically in FIG. 1 exhibits an outer pipe 2 of a highly heat-resistant material, preferably a ceramic material such as aluminum oxide ($Al_2O_3$). Inserted into the lower, open end of the outer pipe 2 is a contact element (not shown in its entire length) of an oxygen-ion conducting material. This element is made of a highly heat-resistant ceramic with desirable oxygen-ion conducting properties, preferably a zirconium oxide doped with yttrium oxide. Contact element 4 is attached inside outer pipe 2 with a crossbolt 6, which can also be made of a ceramic material. The transition zone between the top side of contact element 4 and the lower end of liner pipe 8 is filled with a powder or fine granulate 10 of oxygen-ion conducting material. This granular material is suitably made of the same material as that of contact element 4 and also liner pipe 8. During production of the measuring arrangement, powder 10 is introduced into outer pipe 2 so that it can also possibly fill any gap existing between contact element 4 and outer pipe 2. The liner pipe 8 is then attached in the arrangement such that its lower end is imbedded in powder 10. When the measuring arrangement is operated at high temperatures, powder 10 generally partially sinters together so that a good oxygen-ion conducting connection is made between contact element 4 and liner pipe 8.

A feed pipe 12 for supplying a reference gas with defined oxygen content is positioned with its discharge end reaching into the lower area inside liner pipe 8, the latter being closed at its lower end. Here is the actual measuring zone, which is also filled with a powder of oxygen-ion conducting material. Under the effect of temperature during start-up, the powder partially sinters together into a gas-permeable body designated as solid electrolyte 14. Generally, the platinum reference electrode is conveyed through reference gas feed pipe 12, which also can be referred to as an inner pipe. Furthermore, the feed pipe 12 can also contain the feeds for a thermocouple. This arrangement for the actual measuring area is neither represented in detail nor described here. It can be embodied, for example, as explained in more detail in DE-GM 85 13 976, which can be referred to for additional explanations.

Outer pipe 2 is closed on top by a cover 16 or the like, through which feed pipe 12 for the reference gas extends, and to which a discharge pipe 18 for the reference gas is connected. In discharge pipe 18, there is further placed a bubble counter 20, in which, in a known way, the gas stream can be made visible in the form of bubbles through an amount of liquid.

In the embodiment of FIG. 1, liner pipe 8, which is inside outer pipe 2, is open at its upper end so that the reference gas flowing out of measuring area 21 will also fill annular space 22 between liner pipe 8 and outer pipe 2. The inflow of gases and vapors of the outside atmosphere into this annular space through leaks remaining in the sealed area between contact element 4 and outer pipe 2 can further be avoided by keeping the reference gas at a pressure somewhat higher than that of the surroundings. Under these conditions, the reference gas at point 24 will flow out through possible leaks in the area in which contact element 4 is in use. But, even if this condition were not maintained and external gases penetrated through a leak in the arrangement, these gases cannot reach the interior of the liner pipe 8 because the rising flow of the reference gas in liner pipe 8 prevents this from occurring.

Figure 2:
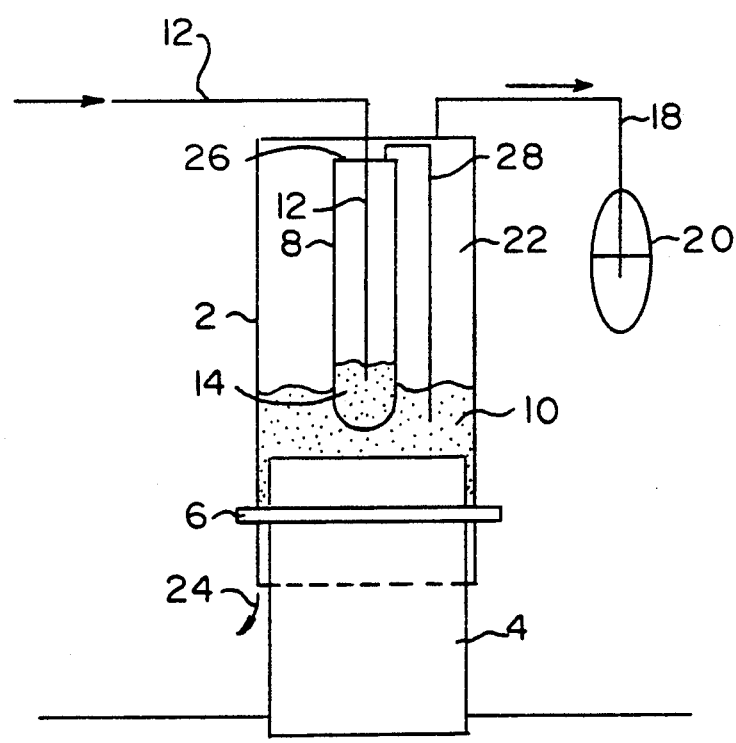
FIG. 2 illustrates another embodiment of a reference electrode arrangement.

The embodiment of FIG. 2 differs from that of FIG. 1 in that liner pipe 8, which is inside outer pipe 2, is itself closed by a cover 26 or the like. The reference gas thus cannot be discharged freely from the liner pipe on top, but rather an overflow pipe 28, connected to cover 26, is provided for the discharge of the reference gas from the liner pipe 8. The outlet end of overflow pipe 28 empties into powdered material 10 located between liner pipe 8 and outer pipe 2. The reference gas, suitable under increased pressure here also, is thus conveyed as protective gas directly to that point at which leaks can exist.

Figure 3:
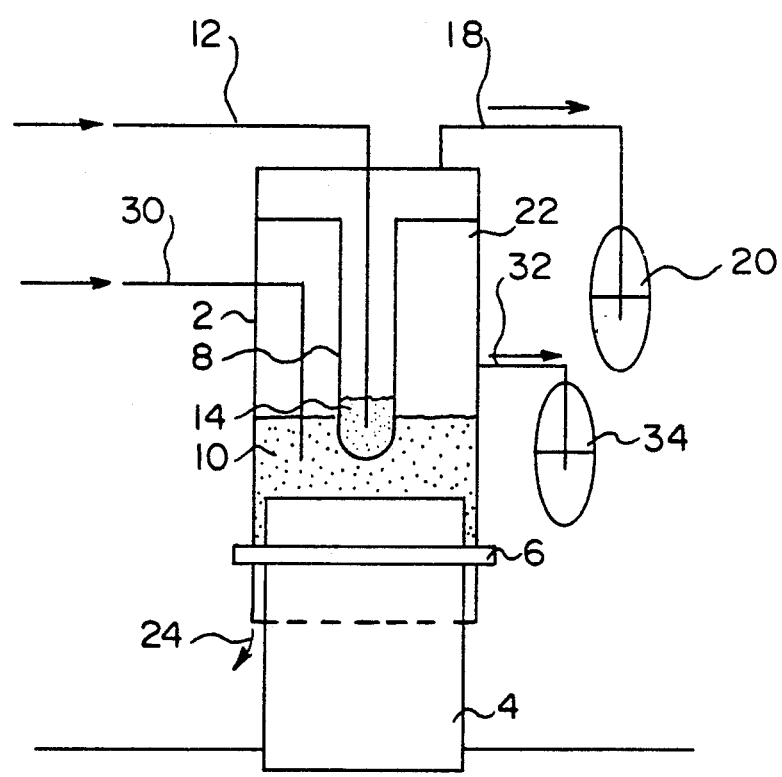
FIG. 3 illustrates a third embodiment of a reference electrode arrangement.

Finally, FIG. 3 shows a third embodiment in which the interior of liner pipe 8 and annular space 22 are completely separated from one another. The interior of liner pipe 8 has a reference gas flowing through it in the same way as with he other embodiments, and this gas is discharged directly from the interior of liner pipe 8. On the other hand, the annular space between liner pipe 8 and outer pipe 2 is provided with inlet connection 30 and outlet connection 32 to permit flushing with an inert protective gas, for example, argon. Feed pipe 30 for the protective gas, in turn, discharges into powdered material 10. Discharge connection 32 is in the upper area of the annular space and is provided, like the discharge pipe for the reference gas, with a bubble counter 34.

The embodiments of the measuring device described guarantee that little or no gases or vapors from the environment which can falsify the measuring values will reach the actual measuring area 21 of the reference electrode arrangement.

From the foregoing description, one skilled in the art can easily ascertain the essential characteristics of this invention and, without departing from the spirit and scope thereof, can make various changes and modifications of the invention to adapt it to various usages and conditions.

In addition, the heating device according to the invention in its various embodiments and attendant features can be incorporated into the reference electrode arrangements disclosed in related, copending U.S. Application Ser. No. 07/420,496.

The entire texts of all applications, patents and publications, cited above and below, are hereby incorporated by reference.

What is claimed is:

1. A measuring device for measuring the oxygen partial pressure in high-temperature, corrosive liquids comprising:
   a measuring electrode adapted for immersion into a corrosive liquid;
   a reference electrode arrangement containing a reference space which is enclosed by an outer pipe made of highly heat-resistant material, said reference space containing a reference electrode and a solid electrolyte of oxygen-ion conducting material, means for introducing a reference gas with defined oxygen content into said reference space, thereby forming a three-phase contact zone, and a contact element with its upper end inserted into the lower, open end of said outer pipe and held there by fastening means, said contact element being adapted for immersion into a corrosive liquid and being made of oxygen-ion conducting material, said contact element also being in oxygen-ion conducting contact with said solid electrolyte in said reference space;
   a liner pipe closed at its lower end and positioned within said outer pipe, said liner pipe containing said reference space and is made of oxygen-ion conducting material; and
   an amount of oxygen-ion conducting powdered material positioned on said upper end of said contact element inserted in said outer pipe, said powdered material being in oxygen-ion conducting contact with said contact element and said lower end of the liner pipe.

2. A measuring device according to claim 1, wherein said contact element is rod-shaped.

3. A measuring device according to claim 1, wherein said amount of oxygen-ion conducting powdered material is sintered.

4. A measuring device according to claim 1, wherein a feed pipe for delivering a reference gas is positioned in said liner pipe with its discharge end in said three-phase contact zone, said liner pipe being open at its upper end and said outer pipe being closed at its upper end, and wherein a discharge pipe for removing a reference gas is connected to said outer pipe.

5. A measuring device according to claim 4, wherein said discharge end of said feed pipe for delivering a reference gas is positioned within said solid electrolyte contained in said liner pipe.

6. A measuring device according to claim 4, wherein said discharge pipe for removing a reference gas is connected to the closed upper end of said outer pipe.

7. A measuring device according to claim 1, wherein said liner pipe is closed at its upper end and a feed pipe for delivering a reference gas is positioned in said liner pipe, an overflow pipe for discharging a reference gas from said liner pipe is connected to an upper area of said liner pipe, the outlet end of said overflow pipe extending into said amount of oxygen-ion conducting powder, the latter being positioned between said liner pipe and said outer pipe, and wherein a discharge pipe for removing a reference gas is connected to the wall of said outer pipe.

8. A measuring device according to claim 7, wherein said discharge pipe for removing a reference gas is connected to an upper region of said outer pipe.

9. A measuring device according to claim 8, wherein said feed pipe for a reference gas is positioned with its discharge end extending into said three-phase contact zone.

10. A measuring device according to claim 9, wherein said feed pipe for a reference gas is positioned with its discharge end extending into said solid electrolyte.

11. A measuring device according to claim 7, wherein said feed pipe for a reference gas is positioned with its discharge end extending into said three-phase contact zone.

12. A measuring device according to claim 11, wherein said feed pipe for a reference gas is positioned with its discharge end extending into said solid electrolyte.

13. A measuring device according to claim 1, wherein the interior of said liner pipe is isolated from the annular space between said liner pipe and said outer pipe, a feed pipe for introducing a reference gas is positioned within said liner pipe and a discharge pipe for removing reference gas is connected to said liner pipe, said discharge pipe being adapted to discharge gas from the interior of said liner pipe directly to the exterior of the measuring device, and wherein feed means and outlet means are provided for flushing said annular space with an inert protective gas.

14. A measuring device according to claim 13, wherein the discharge end of said feed means for introducing an inert protective gas extends into said amount of oxygen-ion conducting powder, the latter being positioned between said liner pipe and said outer pipe.

15. A measuring device according to claim 14, wherein said feed pipe for a reference gas is positioned with its discharge end extending into said three-phase contact zone.

16. A measuring device according to claim 15, wherein said feed pipe for a reference gas is positioned with its discharge end extending into said solid electrolyte.

17. A measuring device according to claim 13, wherein said feed pipe for a reference gas is positioned with its discharge end extending into said three-phase contact zone.

18. A measuring device according to claim 17, wherein said feed pipe for a reference gas is positioned with its discharge end extending into said solid electrolyte.

19. A measuring device according to claim 1, further comprising a discharge pipe for removing a reference gas and a bubble counter connected thereto.

20. A measuring device according to claim 19, further comprising means for introducing an inert protective gas, means for discharging a protective gas and a bubble counter connected to the protective gas discharging means.

21. A measuring device according to claim 1, further comprising means for introducing an inert protective gas, means for discharging a protective gas and a bubble counter to the protective gas discharging means.

22. A method for measuring the oxygen partial pressure in a high temperature, corrosive liquid comprising:
  (a) providing a measuring device comprising:
    a measuring electrode adapted for immersion into a corrosive liquid,
    a reference electrode arrangement containing a reference space which is enclosed by an outer pipe made of highly heat-resistant material, said reference space containing a reference electrode and a solid electrolyte of oxygen-ion conducting material, means for introducing a reference gas with defined oxygen content into said reference space, thereby forming a three-phase contact zone, and a contact element with its upper end inserted into the lower, open end of said outer pipe and held there by fastening means, said contact element being adapted for immersion into a corrosive liquid and being made of oxygen-ion conducting material, said contact element also being in oxygen-ion conducting contact with said solid electrolyte in said reference space,
    a liner pipe closed at its lower end and positioned within said outer pipe, said liner pipe containing said reference space and is made of oxygen-ion conducting material, and
    an amount of oxygen-ion conducting powdered material positioned on said upper end of said contact element inserted in said outer pipe, said powdered material being in oxygen-ion conducting contact with said contact element and said lower end of the liner pipe; and
  (b) determining the oxygen partial pressure of the liquid from the electrical potential difference between the measuring electrode and the reference electrode.

23. The method of claim 22, further comprising measuring the temperature of the liquid and the reference space.

24. A method according to claim 22, wherein said corrosive liquid is a corrosive glass melt or a corrosive salt melt.

25. A method according to claim 22, wherein said corrosive liquid is contained within a container and said measuring electrode is immersed in said corrosive liquid contained in said container.

* * * * *